(12) United States Patent
Li et al.

(10) Patent No.: US 8,460,876 B2
(45) Date of Patent: *Jun. 11, 2013

(54) SCREENING METHODS INVOLVING THE DETECTION OF SHORT-LIVED PROTEINS

(75) Inventors: Xianqiang Li, Palo Alto, CA (US); Xin Jiang, Saratoga, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/288,772

(22) Filed: Nov. 3, 2011

(65) Prior Publication Data

US 2012/0046200 A1   Feb. 23, 2012

Related U.S. Application Data

(63) Continuation of application No. 12/804,733, filed on Jul. 27, 2010, now Pat. No. 8,076,083, which is a continuation of application No. 11/303,037, filed on Dec. 14, 2005, now Pat. No. 7,790,378, which is a continuation of application No. 10/053,516, filed on Jan. 16, 2002, now Pat. No. 7,056,665.

(51) Int. Cl.
*C12Q 1/68* (2006.01)
*C12P 19/34* (2006.01)

(52) U.S. Cl.
USPC ......... 435/6.12; 435/7.1; 435/91.1; 435/91.2; 536/22.1

(58) Field of Classification Search
USPC ................ 435/6.12, 7.1, 91.1, 91.2; 536/22.1
See application file for complete search history.

(56) References Cited

U.S. PATENT DOCUMENTS

| | | | |
|---|---|---|---|
| 6,013,447 | A | 1/2000 | Nilsen et al. |
| 6,221,586 | B1 | 4/2001 | Barton et al. |
| 6,306,600 | B1 | 10/2001 | Kain et al. |
| 6,329,209 | B1 | 12/2001 | Wagner et al. |
| 6,548,249 | B1 | 4/2003 | Anderson et al. |
| 6,610,495 | B1 | 8/2003 | Watt et al. |
| 7,056,665 | B2 | 6/2006 | Li et al. |
| 7,790,378 | B2 | 9/2010 | Li et al. |
| 8,076,083 | B2 * | 12/2011 | Li et al. .......................... 435/6.12 |
| 2002/0007051 | A1 * | 1/2002 | Cheo et al. .................... 536/23.1 |
| 2012/0046200 | A1 * | 2/2012 | Li et al. ............................. 506/12 |

FOREIGN PATENT DOCUMENTS

WO   WO 00/08182 A1   2/2000

OTHER PUBLICATIONS

Bachmair et al. (1986) "In vivo half-life of a protein is a function of its amino-terminal residue," Science, 234:179-186.
Ciechanover et al. (1998) "The ubiquitin-proteasome pathway: the complexity and myriad functions of proteins death," PNAS, 95:2727-2730.
Comrack et al. (1996) "FACS-optimized mutants of the green fluorescent protein (GFP)," Gene, 173:33-38.
Dantuma et al. (2000) "Short-lived green fluorescent proteins for quantifying ubiquitin/proteasome-dependent proteolysis in living cells," Nat. Biotech., 18(5):538-543.
Fenteany et al. (1995) "Inihibition of proteasome activities and sub-unit-specific amino-terminal threonine modification by lactacystin," Science, 268:726-730.
Futcher et al. (1999) "A sampling of the yeast proteome," Mol. Cell. Biol., 19(11):7357-7368.
Ghoda et al. (1989) "Prevention of rapid intracellular degradation of ODC by a carboxyl-terminal truncation," Science, 243:1493-1495.
Glotzer et al. (1991) "Cyclin is degraded by the ubiquitin pathway," Nature, 349:132-137.
Hunt (1991) "Destruction's our delight," Nature, 349:100-101.
Loetscher et al. (1991) "The C terminus of mouse ornithine decarboxylase confers rapid degradation on dihydrofolate reductase," J. Biol. Chem., 266(17):11213-11220.
Pichon et al. (2000) "A method for the large-scale cloning of nuclear proteins and nuclear targeting sequences on a functional basis," Analytical Biochemistry, 284:231-239.
Rechsteiner et al. (1996) "PEST sequences and regulation by proteolysis," Trends Biochem. Sci., 21(7):267-271.
Rogers et al. (1986) "Amino acid sequences common to rapidly degraded proteins: the PEST hypothesis," Science, 234:364-368.
Schimke (1973) "Control of enzyme levels in mammalian tissues," Adv.Enzymol. Relat. Areas. Mol. Biol., 37:135-187.
Tsien (1998) "The green fluorescent protein," Ann. Rev. Biochem., 67:509-544.
Verma et al. (2000) "A proteasome howdunit: the case of the missing signal," Cell, 101:341-344.
Voges et al. (1999) "The 26S proteasome: a molecular machine designed for controlled proteolysis," Ann. Rev. Biochem., 68:1015-1068.

* cited by examiner

*Primary Examiner* — Kenneth R. Horlick
*Assistant Examiner* — Joyce Tung
(74) *Attorney, Agent, or Firm* — Quine Intellectual Property Law Group, P.C.

(57) ABSTRACT

A method is provided for screening for agents that affect protein degradation rates, the method comprising: taking a library of cells, the cells expressing a fusion protein comprising a reporter protein and a protein encoded by a sequence from a cDNA library derived from a sample of cells, the sequence from the cDNA library varying within the cell library; contacting the library of cells with a plurality of agents which may affect protein degradation rates; for each agent, selecting cells in the library which express short-lived proteins based on whether the cells have different reporter signal intensities than other cells in the library, the difference being indicative of the selected cells expressing shorter lived fusion proteins than the fusion proteins expressed by the other cells in the library; and characterizing the fusion proteins expressed by the selected cells for each agent.

23 Claims, 5 Drawing Sheets

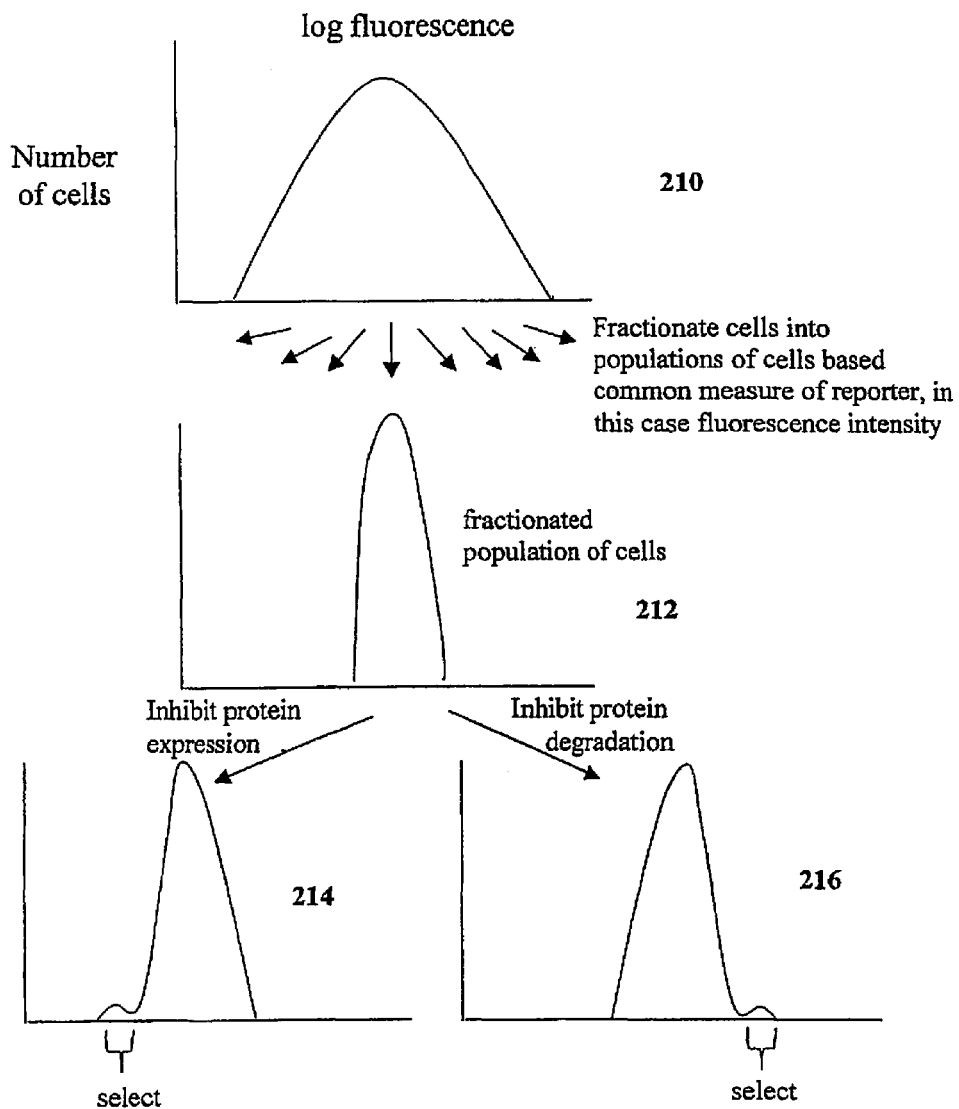

SCREENING METHODS INVOLVING THE DETECTION OF SHORT-LIVED PROTEINS

CROSS-REFERENCE

This application is a continuation application of Ser. No. 12/804,733, filed Jul. 27, 2010, which is a continuation application of Ser. No. 11/303,037, filed Dec. 14, 2005 (now U.S. Pat. No. 7,790,378), which is a continuation application of Ser. No. 10/053,516, filed Jan. 16, 2002 (now U.S. Pat. No. 7,056,665). This application claims priority to and benefit of a each of these applications. Each of these applications is incorporated herein by reference in its entirety.

BACKGROUND OF THE INVENTION

1. Field of the Invention The present invention relates to detecting and characterizing proteins and more specifically to detecting and characterizing short-lived proteins.

2. Description of Related Art

The availability of the entire human genome sequence will revolutionize the way biology and medicine will be explored in the next century and beyond. However, the next big challenge is the development of technologies for the comprehensive analysis of gene expression and the interpretation of the functionality of individual genes and their gene products in the human genome.

A gene is genetic information (i.e., DNA or RNA) that encodes a protein. Proteins, the expression product of genes, have different biological functions within a cell. For example, proteins may act as enzymes, interact with DNA or protein, contribute to the cellular skeleton or possess some other function.

Unfortunately, it is difficult to predict the function of most gene products directly from their gene sequences. As a result, characterization of the biological function of any individual gene product, its association with disease and its pharmaceutical applications are all problems that need to be addressed even after a gene is identified.

One post-genomics field, proteomics, is attempting to bridge the knowledge gap between gene sequences and their biological functions. However, the difficulties facing proteomics are multifaceted. Unlike genes that comprise only four nucleotides and a relatively simple double helical structure, proteins are polymers that comprise different combinations of twenty different amino acids. The amino acid sequence of a protein affects the structure of the protein and hence its function. Some proteins also undergo post-translational modifications that affect their structure and biological activity.

The way in which a protein is expressed also affects the role that the protein plays within a cell. A protein may be expressed or not expressed in response to different conditions, in response to the presence of different agents, and at different levels. Where a protein is expressed within a cell and where the protein is transported after expression also impact the protein's function.

The degradation rate of a protein both affects and evidences its role within a cell. For example, short-lived proteins, i.e., proteins with a short half life, are believed to be very important proteins in cells. It has been commented that the most important proteins will be shown to be short-lived and that most short-lived proteins will be shown to be important.

Examples of proteins that have already been shown to be short-lived include tumor suppressor p53, oncoprotein myc, cyclins, signaling protein IκB, and key biosynthetic enzymes such as ornithine decarboxylase. Their rapid turnover makes it possible for their cellular level to change promptly when synthesis is increased or reduced. Schimke, R. T. (1973) Control of enzyme levels in mammalian tissues. Advanced Enzymology, 37, 135-187.

It is believed that many proteins that turn over rapidly within cells have regulatory roles. For example, transcription factors, cell cycle regulators and metabolic enzymes are all believed to be relatively short-lived proteins.

Identifying whether a given protein is short-lived is very useful toward identifying the protein's role within the cell. Unfortunately however, analysis of whether a given protein is short-lived is currently time-consuming and labor-intensive. The most definitive form of analysis requires pulse-chase labeling cells and immunoprecipitating extracts. In vitro assay of degradation is simpler than in vivo analysis, but an in vitro assay system is difficult to establish and may not fully mimic the degradation of proteins in cells.

Identifying which proteins among all the proteins expressed by a cell are short-lived is highly desirable since it may serve to identify which proteins are the more important proteins to study. However, genome-wide functional screening and systemic. Characterization of cellular short-lived proteins is more complicated than analyzing the lifetime of a single known protein. Identification of short-lived proteins is more difficult because they are degraded more rapidly and tend to be present in lower quantities within the cell. Short-lived proteins are thus harder to detect, isolate and characterize. A need currently exists for a technology that allows for high throughput screening of whether proteins are short-lived.

SUMMARY OF THE INVENTION

The present invention relates to methods, compositions and kits for detecting and characterizing short-lived proteins. Through the present invention, it is possible to perform genome-wide functional screening and systemic characterization of cellular short-lived proteins.

According to one embodiment, a method is provided for selecting cells based on whether the cells express a short-lived-protein, the method comprising: taking a library of cells, the cells in the library expressing a fusion protein comprising a reporter protein and a protein encoded by a sequence from a cDNA library derived from a sample of cells, the sequence from the cDNA library varying within the cell library; modifying a rate of protein expression or degradation by cells in the library; and selecting a population of cells from the library of cells based on the population of cells having different reporter signal intensities than other cells in the library, the difference being indicative of the population of cells expressing shorter lived fusion proteins than the fusion proteins expressed by the other cells in the library.

According to another embodiment, a method is provided for selecting cells based on whether the cells express a short-lived protein, the method comprising: taking a library of cells, the cells in the library expressing a first reporter protein and a fusion protein comprising a second reporter protein and a protein encoded by a sequence from a cDNA library derived from a sample of cells, the sequence from the cDNA library varying within the cell library; modifying a rate of protein expression or degradation by cells in the library; and selecting a population of the cells from the library of cells based on whether the cells have a different normalized reporter signal intensity than other cells in the library, the normalized reporter signal intensity comprising a reporter signal from the fusion protein normalized relative to a reporter signal from the first reporter protein, the difference being indicative of the population of cells expressing shorter lived fusion proteins than the fusion proteins expressed by the other cells in the library.

According to yet another embodiment, a method is provided for selecting cells based on whether the cells express a short-lived protein, the method comprising: taking a library of cells, the cells in the library expressing a fusion protein comprising a reporter protein and a protein encoded by a sequence from a cDNA library derived from a sample of cells, the sequence from the cDNA library varying within the cell library; partitioning the library of cells into populations of cells based on an intensity of a reporter signal from the fusion protein such that cells partitioned into a given population have a reporter signal within a range of reporter signal intensity; modifying a rate of protein expression or degradation by cells for a given population of cells; and selecting a subpopulation of cells from the given population of cells based on whether the cells have a different reporter signal intensity than the other cells in the given population, the difference being indicative of the subpopulation of cells expressing shorter lived fusion proteins than the fusion proteins expressed by the other cells in the given population.

According to yet another embodiment, a method is provided for selecting cells based on whether the cells express a short-lived protein, the method comprising: taking a library of cells, the cells in the library expressing a first reporter protein and a fusion protein comprising a second reporter protein and a protein encoded by a sequence from a cDNA library derived from a sample of cells, the sequence from the cDNA library varying within the cell library; partitioning the library of cells into populations of cells based on an intensity of a reporter signal from the fusion protein such that cells partitioned into a given population have a reporter signal within a range of reporter signal intensity; modifying a rate of protein expression or degradation by cells for a given population of cells; and selecting a subpopulation of the cells from the population of cells based on whether the cells have a different normalized reporter signal intensity than the other cells in the population, the normalized reporter signal intensity comprising a reporter signal from the fusion protein normalized relative to a reporter signal from the first reporter protein, the difference being indicative of the subpopulation of cells expressing shorter lived fusion proteins than the fusion proteins expressed by the other cells in the given population.

According to another embodiment, a method is provided for selecting cells based on whether the cells express a short-lived protein, the method comprising: forming a construct library encoding a library of fusion proteins, the fusion proteins comprising a reporter protein and a protein encoded by a sequence from a cDNA library derived from a sample of cells; transducing or transfecting the construct library into cells to form a library of cells which express the library of the fusion proteins; screening the transduced or transfected cells for cells which express the fusion protein; partitioning the screened cells into populations of cells based on an intensity of a reporter signal from the fusion protein such that cells partitioned into a given population have a reporter signal within a range of reporter signal intensity; modifying a rate of protein expression or degradation by cells in the given population; and selecting a subpopulation of the cells from the given population of cells based on whether the cells have a different reporter signal intensity than the other cells in the given population, the difference being indicative of the subpopulation of cells expressing shorter lived fusion proteins than the fusion proteins expressed by the other cells in the given population.

According to this method, the library of cells may optionally further express an internal standard protein having a different reporter signal than the reporter protein, and selecting the subpopulation of cells may optionally further comprise normalizing the reporter signal from the fusion protein using the reporter signal from the internal standard protein.

According any of the above methods, screening may be performed using a flow cytometer. In such instances, the reporter protein is preferably a protein that can be detected by the flow cytometer and used to screen the cells.

According any of the above methods, the reporter protein may be a fluorescent protein. For example, the reporter protein may be a green fluorescence protein (GFP), an enhanced green fluorescence protein (EGFP), or a red fluorescent protein. The reporter protein may also be beta-galactosidase.

According any of the above methods, screening and partitioning may be performed using a flow cytometer.

Also according any of the above methods, when the reporter protein is a fluorescent protein and partitioning is performed, the range of reporter signal intensity is optionally a half log interval of fluorescence.

Also according any of the above methods, when the reporter protein is a fluorescent protein and partitioning is performed, a given population that is formed may optionally have a modal brightness that differs from another population by a factor of at least 3.

Also according any of the above methods, when the reporter protein is a fluorescent protein and partitioning is performed, partitioning may comprise partitioning the screened cells into at least 4 populations of cells where the reporter signal intensities of cells within a given population do not overlap with the reporter signal intensities of cells within another population of cells.

Also according any of the above methods, when protein expression is inhibited, selecting a subpopulation of the cells from the given population of cells may be based on cells having a reduced reporter signal intensity than the other cells in the given population.

Also according any of the above methods, when protein expression is inhibited, selecting a subpopulation of the cells from the given population of cells may be based on cells having less than half reporter signal intensity than the other cells in the given population.

Also according any of the above methods, when protein degradation is inhibited, selecting a subpopulation of the cells from the given population of cells may be based on cells having an increased reporter signal intensity than the other cells in the given population.

Also according any of the above methods, when protein degradation is inhibited, selecting a subpopulation of the cells from the given population of cells may be based on cells having more than twice the reporter signal intensity than the other cells in the given population.

Also according any of the above methods, the selected subpopulation of the cells may optionally be subjected to one or more additional rounds of selection, each round of selection comprising modifying a rate of protein expression or degradation by the cells, and selecting a further subpopulation of the cells based on whether the cells having a different reporter signal intensity than the other cells in the given population.

Also according any of the above methods, the selected subpopulation of the cells may optionally be subjected to one or more additional rounds of selection such that at least one round of selection comprises inhibiting protein expression and at least one round of selection comprises inhibiting protein degradation.

Also according any of the above methods, the selected subpopulation of cells may optionally be further selected, at least partially, by culturing cells separately and individually monitoring how the reporter signal of each cell changes in response to protein synthesis or protein degradation being inhibited.

Also according any of the above methods, the selected subpopulation of cells may optionally be further selected, at least partially, by culturing cells separately and individually monitoring how the reporter signal of each cell changes using a fluorescent plate reader.

Also according any of the above methods, the methods may optionally further comprise analyzing whether the fusion protein of the selected cells is short-lived by a pulse-chase analysis.

Also according any of the above methods, the method may optionally further comprise analyzing whether the fusion protein of the selected cells is short-lived by radiolabelling the expressed fusion protein; immunoprecipitating the expressed fusion protein with anti-GFP antisera; and analyzing the immunoprecipitate by SDS-PAGE and autoradiography.

Also according any of the above methods, the method may optionally further comprise determining the nucleic acid sequences of the fusion proteins.

Also according any of the above methods, the method may optionally further comprise determining the protein sequences of the fusion proteins.

Also according any of the above methods, the method may optionally further comprise analyzing whether the portion of the fusion protein encoded by the sequence from the cDNA library is short-lived when expressed independent of the reporter protein.

Methods are also provided for monitoring the effects that different growth conditions have on expression of short-lived proteins In one embodiment, the method comprises: exposing samples of cells to different growth conditions; forming cDNA, libraries from the sample of cells after exposure to the different growth conditions; forming a library of cells for each cDNA library, the cells in the library expressing a fusion protein comprising a reporter protein and a protein encoded by a sequence from the cDNA library derived from a sample of cells, the sequence from the cDNA library varying within the cell library; for each library of cells: identifying cells within the library that express fusion proteins that are degraded in vivo more rapidly than other fusion proteins, and characterizing fusion proteins expressed by the identified cells; and comparing which fusion proteins are characterized for each library of cells, differences in the characterized fusion proteins indicating differences in the short-lived proteins expressed by when the cells are exposed to the different agents.

In one variation, identifying cells within the library that express fusion proteins that are degraded in vivo more rapidly than other fusion proteins comprises modifying a rate of protein expression or degradation by the cells, and selecting a population of the cells based on whether the cells have a different reporter signal intensity than the other cells after the rate of protein expression or degradation has been modified.

In another embodiment, the method comprises: exposing samples of cells to different conditions; forming cDNA libraries from the sample of cells after exposure to the different growth conditions; forming a library of cells for each cDNA library, the cells in the library expressing a fusion protein comprising a reporter protein and a protein encoded by a sequence from the cDNA library derived from a sample of cells, the sequence from the cDNA library varying within the cell library; for each library of cells: partitioning the library of cells into populations of cells based on an intensity of a reporter signal from the fusion protein such that cells partitioned into a given population have a reporter signal within a range of reporter signal intensity, modifying a rate of protein expression or degradation by the cells for a given population of cells, selecting a subpopulation of the cells from the given population of cells based on whether the cells have a different reporter signal intensity than the other cells in the given population, and characterizing fusion proteins expressed by at least a portion of the selected cells; and comparing which fusion proteins are characterized for each library of cells, differences in the characterized fusion proteins indicating differences in the short-lived proteins expressed by when the cells are exposed to the different agents.

In one variation, exposing the samples of cells to different conditions comprises exposing the cells to different agents.

A method is also provided for screening for differences in short-lived proteins expressed by first and second cell samples.

In one embodiment, the method comprises: forming cDNA libraries for first and second samples of cells; forming a library of cells for each cDNA library, the cells in the library expressing a fusion protein comprising a reporter protein and a protein encoded by a sequence from the cDNA library derived from a sample of cells, the sequence from the cDNA library varying within the cell library; for each library of cells: identifying cells within the library that express fusion proteins that are degraded in vivo more rapidly than other fusion proteins, and characterizing fusion proteins expressed by the identified cells; and comparing which fusion proteins are characterized for each library of cells, differences in the characterized fusion proteins indicating differences in the short-lived proteins expressed by the first and second samples cells.

In another embodiment, the method comprises: forming cDNA libraries for first and second samples of cells; forming a library of tells for each cDNA library, the cells in the library expressing a fusion protein comprising a reporter protein and a protein encoded by a sequence from the cDNA library derived from a sample of cells, the sequence from the cDNA library varying within the cell library; for each library of cells: partitioning the library of cells into populations of cells based on an intensity of a reporter signal from the fusion protein such that cells partitioned into a given population have a reporter signal within a range of reporter signal intensity, modifying a rate of protein expression or degradation by the cells for a given population of cells, selecting a subpopulation of the cells based on whether the cells have a different reporter signal intensity than other cells after the rate of protein expression or degradation has been modified, and characterizing fusion proteins expressed by at least a portion of the selected cells; and comparing which fusion proteins are characterized for each library of cells, differences in the characterized fusion proteins indicating differences in the short-lived proteins expressed by the first and second samples cells.

BRIEF DESCRIPTION OF THE DRAWINGS

FIG. 2B illustrates exemplary fluorescence intensity plots for the process illustrated in FIG. 2A.

DETAILED DESCRIPTION OF THE INVENTION

Figure 1:
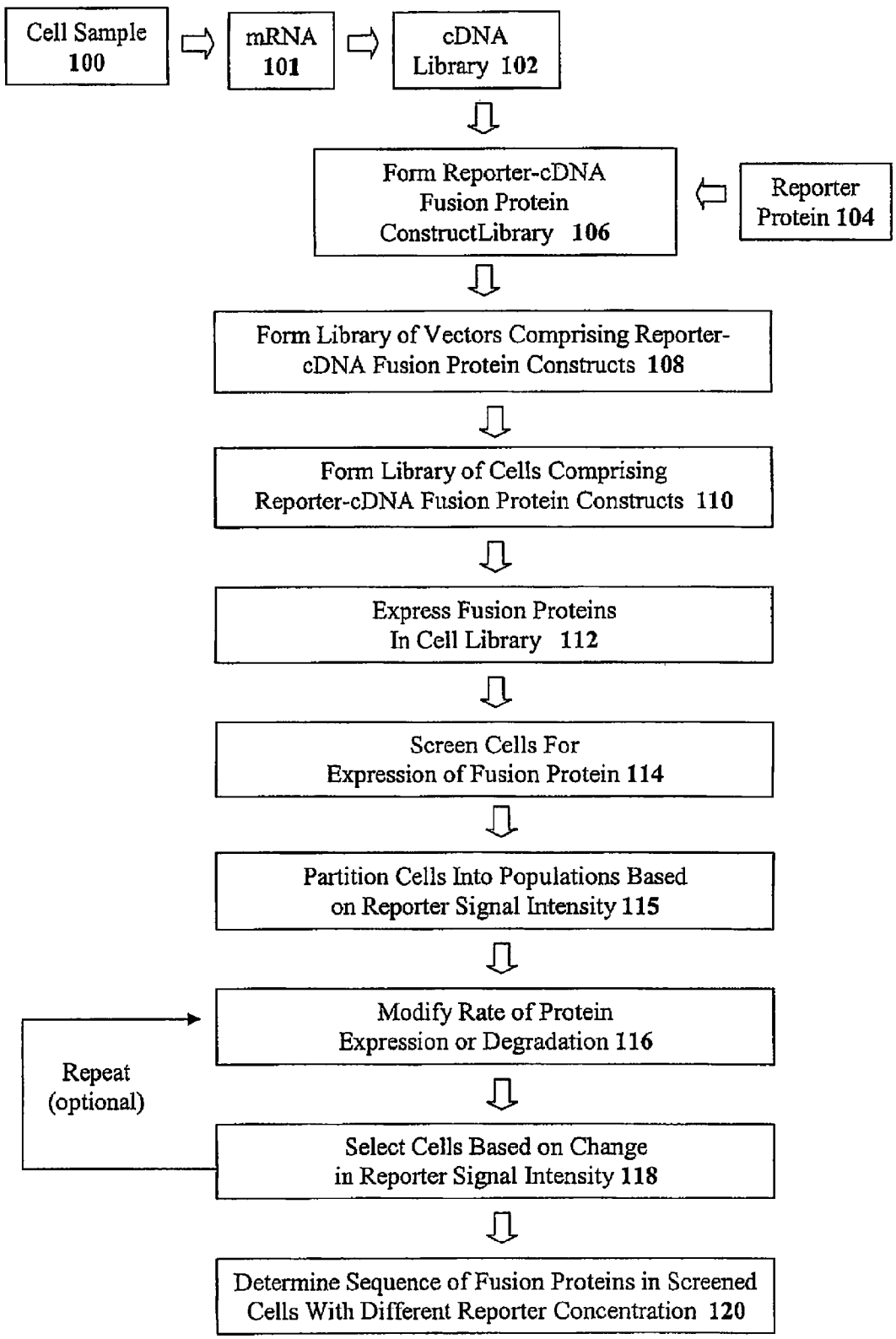
FIG. 1 provides a general overview of how short-lived proteins encoded by DNA from a cDNA library may be detected and characterized in a high-throughput manner according to the present invention.

Proteins that degrade more rapidly than other proteins in vivo (i.e., proteins with short half lives) are believed to be functionally significant and hence proteins whose study should be prioritized. By identifying these proteins and better understanding their function and how their expression and degradation are regulated, a myriad of therapeutic applications can be developed. For example, it may prove therapeutically advantageous to induce or inhibit expression of certain of these proteins for selected disease states. It may also prove therapeutically advantageous to develop inhibitors for certain of these proteins for selected disease states. It may also prove therapeutically advantageous for certain disease states to increase or decrease the half life of these proteins in vivo, for example by stimulating or inhibiting the regulatory pathway controlling the degradation of these proteins.

As will be described herein, the present invention provides high throughput methods that allow short-lived proteins to be identified and studied more efficiently. For example, the present invention relates to methods for identifying which proteins expressed by a given cell sample are degraded more rapidly than other proteins also expressed by the cell sample. The more rapidly degraded proteins are referred to herein as "short-lived proteins." By understanding which proteins are short-lived, these proteins may be targeted for further study. Expression of at least some short-lived proteins is regulated. The present invention also relates to methods for identifying short-lived proteins whose expression is affected by particular conditions. By knowing what conditions affect the expression of different short-lived proteins, therapeutic applications may be developed to induce or inhibit their expression.

The degradation rate of some proteins may also be regulated. The present invention relates to methods for identifying short-lived proteins whose degradation rate in vivo is affected by particular conditions. By knowing what conditions affect the degradation of different short-lived proteins, how protein degradation of particular short-lived proteins is regulated can be better understood. Further, therapeutic applications can be developed as a result of better understanding bow degradation of these proteins is regulated and what agents influence their degradation.

Compositions and kits for use in combination with the various methods of the present invention are also provided.

Advantageously, the methods of the present invention are high-throughput methods in the sense that they can be used to perform genome-wide functional screening and systemic characterization of groups of cellular proteins as short-lived proteins. Because short-lived proteins are likely to be functionally significant, the ability to systematically identify certain proteins as being short-lived greatly assists in identifying which are the more important proteins being expressed. Given that many short-lived proteins are regulatory proteins, knowing which proteins are short-lived also helps to determine the functional significance of these proteins.

Using the technology of the present invention, functional identification of important regulatory proteins from the entire human genome is made possible in a high-throughput screening format. With this technology, human genes can be systematically screened and new genes can easily be identified from expression libraries. Because of their importance in biological function, these short-lived proteins have a great potential in drug discovery.

As will become evident by the following description of the invention, the methods of the invention advantageously allow one to differentiate and identify short-lived proteins from longer lived proteins without knowing in advance which proteins are short-lived and without knowing in advance the sequences of the various short-lived proteins that will ultimately be identified.

FIG. 1 provides a general overview of how short-lived proteins may be detected and characterized in a high-throughput manner according to the present invention.

As illustrated, mRNA 101 is obtained from a cell sample 100. A cDNA library 102 is then formed from the mRNA 101. The cDNA library 102 and a sequence encoding a reporter protein 104 are combined to form a construct library 106 encoding fusion proteins, each fusion protein comprising a protein encoded by a sequence from the cDNA library and the reporter protein.

A vector library 108 is formed from the construct library 106 in order to introduce the fusion protein constructs into a cell line. Introduction of the vector library may be performed by transduction or transfection, depending on the nature of the vector and the nature of the cell line.

A library of cells 110, once formed using the vector library, express the library of fusion proteins. The library of expressed fusion proteins comprise short-lived fusion proteins and a larger number of longer-lived fusion proteins. Described herein is a process for selecting cells from the library that express fusion proteins that behave as short-lived proteins over the larger group of cells that express fusion proteins that behave as longer-lived proteins.

As seen in step 112, the fusion proteins are expressed by the library of cells. The cells are then screened 114 for expression of the fusion protein based on detection of the reporter signal. The screen 114 serves to remove cells that do not exhibit a reporter signal. As a result, cells that express a fusion protein are separated from cells that either did not receive a construct or received a non-productive construct.

The reporter protein should be a protein whose expression may be detected in vivo. A variety of such proteins may be used, most commonly fluorescent proteins such as green fluorescence protein (GFP) and enhanced green fluorescence protein (EGFP) which may be readily detected and used to screen the cells by a flow cytometer.

After the cell library is screened 114, the screened cells are partitioned 115 into populations of cells where the measured reporter signal from the fusion protein in a given population is within a predetermined range. For example, if the reporter is fluorescent, the cells are grouped into populations where all the cells in a given population fluoresce within a given range of fluorescence intensity.

For a given population of cells, the rate at which protein expression or degradation occurs is then modified 116. A subpopulation of the cells is then selected 118 from the given population of cells based on, those cells having different reporter signal intensities than the other cells in the given population, the difference in reporter signal intensities being indicative of the subpopulation of cells expressing shorter lived fusion proteins than the fusion proteins expressed by the other cells in the given population. The subpopulation of cells selected will typically represent a minority of the cells of the given population.

Figure 2A:
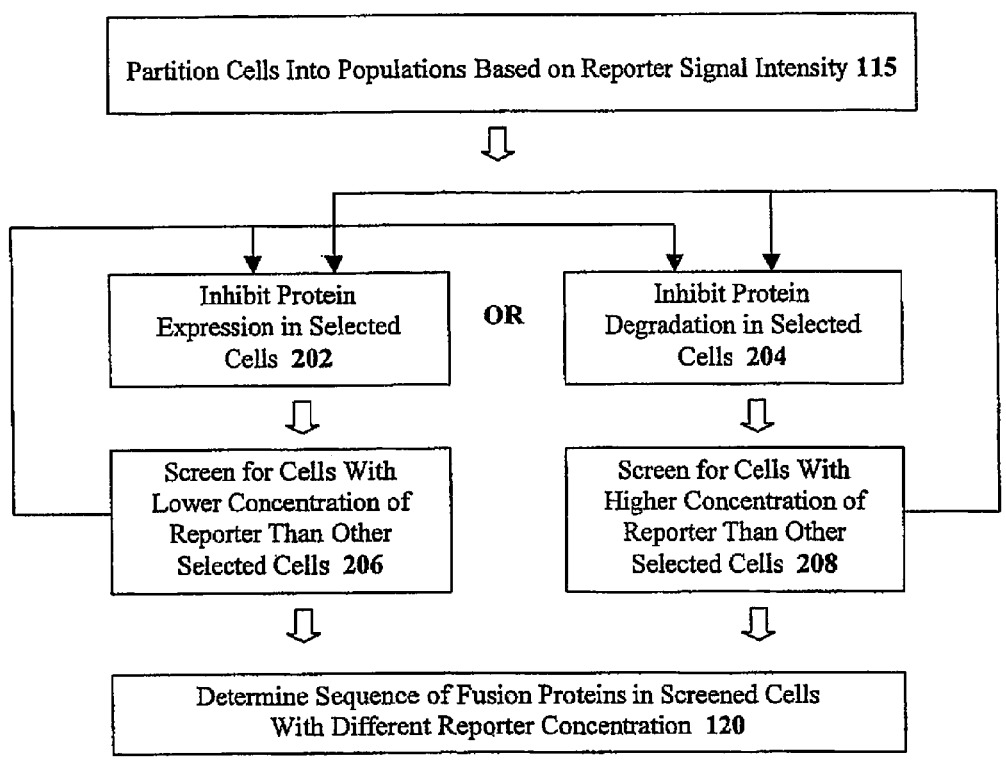
FIG. 2A illustrates a process of inhibiting either protein expression or degradation and then screening for a subpopulation of cells that have a different reporter protein signal.

The process of partitioning the cells into populations 115, modifying the rate of protein expression or degradation 116, and selecting a subpopulation of cells based on reporter signal intensity 118 is described in more detail in regard to FIGS. 2A and 2B.

Referring to partitioning the cells into populations 115, FIG. 2B illustrates a plot of fluorescence for cells expressing fusion proteins where the reporter is fluorescent. As illustrated, the different cells have a range of fluorescence intensities 210. In order to better monitor changes in fluorescence intensities for individual cells, the cells are fractionated into populations of cells where cells in a given population are all within a narrower range of fluorescence. For example, the fluorescence plot of one fractionated population of cells 212 is shown in FIG. 2B.

Referring to the step of modifying the rate of protein expression or degradation 116 of FIG. 1, it is noted that short-lived proteins are degraded faster than other proteins. As a result, when protein expression is inhibited, the concentration of short-lived protein in the cell will decrease at a more rapid rate than longer-lived proteins because protein expression is not replacing the short-lived proteins. As a result, the reporter signal intensity in cells expressing a short-lived fusion protein will decrease more rapidly than other cells within a given population. Referring to FIG. 2A, it is possible to inhibit protein expression 202 and then select cells 206 expressing a short-lived fusion protein by selecting those cells whose reporter signal is lower than other cells in the cell population. Exemplary fluorescence intensity plots for this process are illustrated in FIG. 2B where a population of cells that initially had a common fluorescence intensity (as shown in plot 212) has separated over time into two populations where a small sub-population has a lower fluorescence intensity after protein synthesis is inhibited (as shown in plot 214).

When protein degradation is inhibited in step 116 of FIG. 1, because short-lived proteins are degraded faster than other proteins, the concentration of short-lived proteins will increase at a more rapid rate than will longer-lived proteins. As a result, the reporter signal of cells expressing a fusion protein comprising a short-lived protein within a given population will increase more rapidly than cells expressing a fusion protein comprising a longer-lived protein. Referring again to FIG. 2A, it is possible to inhibit protein degradation 204 and then select those cells 208 that express a short-lived fusion protein by selecting those cells whose reporter signal is higher than other cells in the cell population. Exemplary fluorescence intensity plots for this process are illustrated in FIG. 2B where a population of cells that initially had a common fluorescence intensity (as shown in plot 212) has separated over time into two populations where a small sub-population has a higher fluorescence intensity after protein degradation is inhibited (as shown in plot 216).

As illustrated in FIGS. 1 and 2A, the process of inhibiting either protein expression or degradation and then screening for a subpopulation of cells which have a different reporter protein signal may be performed once or repeated one or more times in order to more carefully select cells expressing short-lived fusion proteins. For example, in one variation, at least one selection is performed after inhibiting protein expression and at least one selection is performed after inhibiting protein degradation.

Optionally, the cells selected as having a different reporter signal than other cells in the population in response to protein synthesis or protein degradation being inhibited may be further evaluated prior to sequencing the fusion proteins. For example, as described herein, different cells may be cultured separately and then individually monitored for how their reporter signal changes in response to protein synthesis or protein degradation being inhibited. By monitoring the reporter signal behavior of different cells separately, it is possible to more carefully evaluate whether a given fusion protein is being degraded as would a protein with a relatively shorter half life. As a result, a more careful cell selection may be performed.

After cells believed to encode short-lived fusion proteins are finally selected, the nucleic acid and protein sequences of the fusion proteins may be determined.

Once the sequences of the fusion proteins and the cDNA encoding them are known, a variety of additional analyses may be performed. For example, database searches may be performed based on the cDNA or protein sequences in order to determine whether the cDNA sequence and/or the protein encoded by the cDNA sequence are already known. In some instances, the proteins identified by the above selection process will be novel. Even if some of the proteins are already known, their cDNA sequences may not have been known. Furthermore, the fact that these proteins are degraded more rapidly is valuable information since it indicates that these proteins may be regulatory proteins.

As can be seen from the above description, the process of the present invention allows one to screen an entire cDNA library for proteins whose difference in degradation rates evidence that these proteins are short-lived. The proteins and their cDNA need not be known prior to performing the process of the present invention or known even when performing the process. Rather, only those proteins that are likely to be short-lived proteins need to be sequenced according to the present invention.

As can also be seen, the method of the present invention allows the discovery of various valuable pieces of information that all incrementally help to fill the proteomics knowledge gap.

By being able to rapidly identify proteins as being short-lived in combination with the cDNA sequences encoding the proteins, a myriad of applications arise, some of which are described herein in further detail. For example, by determining which proteins are short-lived, arrays comprising cDNA for the short-lived proteins can be produced which allow one to rapidly monitor how expression of different short-lived proteins changes under different conditions.

The design, operation and applications for the present invention will now be described in greater detail.

1. Formation of Reporter-cDNA Fusion Protein Construct Library

In order to systematically clone all genes whose products may be short-lived, a fusion expression library is formed by combining a sequence encoding a reporter protein with a cDNA library formed from mRNAs isolated from a sample of cells. A wide variety of methods are known in the art for forming a cDNA library from mRNA isolated from a cell sample. Any of these methods may be used in the present invention.

In one embodiment, an agent such as Trizol reagent (Gibco BRL) is used to isolate total RNA from cells or a tissue sample. Oligo (dT) columns is then used to purify poly $(A)^4$ RNAs. First-strand cDNA synthesis may then be primed from poly $(A)^+$RNAs by oligo dT primers. A cDNA library may then be constructed using SMART (Switching Mechanism at 5'end of RNA template) library construction technology from CLONTECH. This method simultaneously employs the two intrinsic properties of M-MLV, namely RT—reverse transcription of mRNA template and template switching activity. The technique allows two different restriction sites to be added to the anchor and oligo dT primers, to conduct directional cloning cDNAs.

Optionally, the oligo(dT) primer may include an BamH I site and an EcoR I site may be introduced into the anchor. First strand synthesis is then performed with 5-methyl dCTP, producing hemimethylated cDNA, with the unmethylated BamH I site on the linker/primer. Second-strand cDNA is generated with the unmethylated EcoR I site on the anchor as a primer, using an enzyme mixture of *E. coli* DNA polymerase, RNA ligase and RNase H. The double-stranded cDNA is digested with appropriate restriction enzymes to generate two different sticky ends. After size fractionation, the cDNA may be directionally cloned into expression vectors. Compared to cDNA cloned nondirectionally, libraries made according to this method are more likely to make functional fusion proteins for expression screening.

The reporter protein may be any protein that enables cells expressing the reporter protein as part of a fusion protein to be screened in vivo. The sequence encoding the reporter protein may be 3' or 5' relative to the sequence from the cDNA library.

In one embodiment, the reporter protein is an autofluorescent protein. A unique feature of autofluorescent proteins is their ability to be detected without any substrate or cofactor. Using an autofluorescent protein as the reporter, fluorescence associated with single cells can be analyzed by fluorescence activated cell sorting (FACS), a technology easily adapted to high throughput screening. Galbraith, D. W., Anderson, M. T. and Herzenberg, L. A. (1999) Flow cytometric analysis and FACS sorting of cells based on GFP accumulation. *Methods Cell Biol*, 58, 315-41. Thus, FACS can be used for analysis of the large number of human genes.

Green fluorescent protein (GFP) is an example of an autofluorescent protein. GFP from the jellyfish *Aequorea victoria* has been widely used to study gene expression and protein localization. Tsien, R. Y. (1998) The green fluorescent protein. *Annu Rev Biochem*, 67, 509-44. GFP has also been found in a variety of other organisms including *Renilla*.

Enhanced GFP (EGFP) is a mutant of GFP with 35-fold increase in fluorescence, which dramatically improves the detection of GFP. The fluorescence of GFP is dependent on the key sequence Ser-Tyr-Gly (amino acids 65 to 67) that undergoes spontaneous oxidation to form a cyclized chromophore. Enhanced GFP (EGFP) contains mutations of Ser to Thr at amino acid 65 and Phe to Leu at position 64, and is encoded by a gene with human-optimized codons. Cormack, B. P., Valdivia, R. H. and Falkow, S. (1996) FACS-optimized mutants of the green fluorescent protein (GFP). *Gene*, 173, 33-8.

A wide variety of methods are known in the art for forming a fusion protein library between a first protein (in this case the reporter protein) and sequences from the cDNA library. In one embodiment, the fusion protein libraries are constructed by fusing cDNA to the C terminus of the reporter protein, such as GFP or EGFP. Optionally, pEGFP-N1, N2, and N3 (CLONTECH) may be used to express GFP fusion proteins. pEGFP-N1, N2, and N3 are a set of vectors with three open reading frames. The vectors contain the CMV promoter, multiple cloning sites (MCS), the EGFP gene and an SV40 poly A site. The MCS with three reading frames allows genes to be cloned 5' relative to the EGFP gene. The expression vectors also contain the SV40 origin of replication, which allows extra-chromosomal replication and facilitate recovery from cells, such as COS-7, that express the SV40 large T antigen.

2. Formation of Vector Library Comprising Reporter-cDNA Fusion Protein Constructs A variety of different vectors may be formed to transfer the library of constructs into a cell line. These vectors may introduce the constructs into the cell line by transfection or transduction. For example, the library of constructs may be ligated into expression vectors such as pd1EGFP, pd2EGFP, and pd4EGFP which are each commercially available mammalian expression vectors that code for the fluorescence protein EGFP. These constructs are made from pEGFP-C1 with the C-terminal fusion of the degradation domain of mouse ornithine decarboxylase and demonstrated in cells with a short half-life, a range from 1 hour to 4 hours. To normalize the transfection, a second reporter construct, such as beta-galactosidase, can be co-transfected with the fluorescence protein construct under the control of the same or a different promoter.

3. Formation of Library of Cells Comprising Reporter-cDNA Fusion Protein Constructs The library of vectors encoding the reporter-cDNA fusion proteins are then introduced into a cell line to produce a library of cells which express the reporter-cDNA fusion proteins. Preferably, the cell library formed has a diversity of at least $>10^4$, more preferably $>10^5$, and most preferably a diversity of at least $>10^6$.

The recipient cell line of the vector library is preferably of a same genus as the sample of cells from which the cDNA library is derived. For example, a fusion protein library formed from cDNA derived from mammalian cells is preferably formed in a mammalian cell line. Similarly, a fusion protein library comprising cDNA derived from plant cells is preferably formed in a plant cell line.

In one embodiment, when the cDNA library is derived from a mammalian cells, the recipient cell line of the vector library is CHO cells or COS-7 cells. When a pd2EGFP vector is employed, it is desirable to use COS-7 cells because these cells express the SV40 large T antigen which results in high-copy extra-chromosomal replication of the pd2EGFP vector.

Once the library of cells is formed, the library is allowed to express the fusion proteins and is then screened for whether the fusion protein is being expressed. For example, when the reporter is a fluorescent protein, such as GFP or EGFP, the cells can be efficiently screened by FACS sorting. This allows one to easily separate transformed or transfected cells from untransformed or untransfected cells and cells that were transformed or transformed by non-productive constructs.

4. Sorting Cell Library Into Populations Based on Reporter Signal Intensity

The library of cells formed by transfecting or transducing a cell line with vectors encoding a library of fusion proteins will have a distribution of reporter signal intensities. For example, when the reporter is a fluorescent protein, a cell population with an approximately log-normal fluorescence histogram distribution may have a fluorescence distribution of 4 logs to the base 10.

According to the present invention, cells that are likely to encode short-lived proteins are selected by detecting changes in the cells' reporter signal intensity over time. By narrowing the distribution of reporter signal intensities within a given population of cells, it is possible to detect changes in the reporter signal intensities of individual cells within the population of cells. Therefore, prior to inhibiting protein synthesis or protein degradation, the cell library is first divided into populations, each with a distinct and narrow distribution of reporter signal intensities. Together, the populations cover the full dynamic range of the library of cells. In one variation, the cell library is divided into 2, 3, 4, 5, 6, 7, 8, 9, 10 or more populations.

When a fluorescent reporter protein is employed, FACS fractionation may be used to divide the library into separate populations where each population has a distinct and narrow fluorescence brightness distribution. Optionally, each population may be fractionated to within a half-log interval of fluorescence. This would cause each population to have a modal brightness that differs from that of an immediately adjacent population by a factor of about 3.3.

After the library is divided into separate populations with a narrower distribution of reporter signal intensities than the library, the distribution of reporter signal intensities for each population may be checked to confirm that the cells in a given population have the desired distribution of reporter signal intensities. If the population is not found to have the desired reporter signal intensity distribution, the population may be fractioned again. This process may be repeated as many times as necessary in order to produce populations of cells which each have the desired distribution of reporter signal intensities within the population.

5. Selecting Cells By Inhibiting Protein Expression and/or Protein Degradation

Once separate populations of cells are formed, each population is separately analyzed for the presence of short-lived proteins.

For a given population, a subpopulation of cells is selected based on time-dependent changes in the reporter signal intensity of the cells within the population in response to inhibiting either protein synthesis or protein degradation. This selection process may be repeated multiple times where the subpopulation of cells formed in a given round is further screened and narrowed in a later selection round. Optionally, the multiple rounds of selection include inhibiting protein synthesis and protein degradation in separate rounds. When both types of inhibition are performed in separate selections, a finer screen is accomplished.

In one embodiment, cells that have been partitioned into a population of cells having a desired distribution of reporter signal intensities are selected based on how inhibition of protein synthesis reduces the reporter signal intensity. A variety of different agents may be used to inhibit protein synthesis. Examples of such agents include, but are not limited to cycloheximide.

When protein synthesis is reduced or blocked, short-lived proteins are more readily degraded. Hence, the signal of the reporter in the fusion protein decreases. By selecting those cells whose reporter signal decreases more rapidly than other cells, one is able to detect cells expressing a short-lived fusion protein.

In one embodiment, cells that have been partitioned into a population of cells having a desired distribution of reporter signal intensities are selected based on how inhibition of protein degradation increases the reporter signal intensity. A variety of different protein degradation inhibiters may be used. One such inhibitor is lactacystin, a specific proteasome inhibitor. Fenteany, G., Standaert, R. F., Lane, W. S., Choi, S., Corey, E. J. and Schreiber, S. L. (1995) Inhibition of proteasome activities and subunit-specific amino-terminal threorine modification by lactacystin. Science, 268, 726-731; Omura, S., Fujimoto, T., Otoguro, K., Matsuzaki, K., Moriguchi, R., Tanaka, H. and Sasaki, Y. (1991) Lactacystin, a novel microbial metabolite, induces neuritogenesis of neuroblastoma cells. *J Antibiot* (Tokyo), 44, 113-6.

When degradation of short-lived proteins is inhibited, the concentration of short-lived proteins increases within the cell. This results in the signal of the reporter in the fusion protein increasing. By selecting those cells whose reporter signal increases more rapidly than other cells, one is able to detect cells expressing a fusion protein comprising a short-lived protein.

Exposure to agents that inhibit protein synthesis and protein degradation should be controlled so that live cells may be recovered and further processed. Hence, exposure to inhibitors should be limited to durations that are consistent with survival. Also, it is recognized that prolonged exposure could induce a secondary cellular response that produces alterations in signal intensity from causes other than protein turnover. This could result in a false-positive background. As discussed herein, a second reporter protein may be used as an internal standard to counter these potential alterations in reporter signal intensity.

The duration desirable for inhibiting protein synthesis or protein degradation is dependent upon how great a change in the signal intensity of the reporter is to be detected. It is also dependent upon the desired maximum half life of the proteins to be detected. For example, cells may be selected which show at least a 2×, 4×, 6×, or 8× change in reporter signal intensity. This change in reporter signal intensity may occur over varying lengths of time, such as within 1 hour, 2 hours, 3 hours, etc. In the case of inhibiting protein synthesis, the half life of a protein would be expected to equal the time required for the reporter signal intensity associated with the protein to decrease by 50%, assuming no pharmacological lag. Hence, a protein with 2 times less reporter signal intensity after an hour would be expected to have a half life of about 1 hour. Similarly, a protein with 4 times less reporter signal intensity after two hours and a protein with 8 times less reporter signal intensity after three hours would both be expected to have a half life of about 1 hour, assuming no pharmacological lag.

As described above, prior to inhibiting protein synthesis or protein degradation, the cell library is divided into populations, each with a distinct and narrow distribution of reporter signal intensities. When a fluorescent reporter protein is used, each population will have a distinct and narrow fluorescence brightness distribution. Together, the populations cover the full dynamic range of the library of cells.

Each population is subjected individually to one or more protein synthesis or protein degradation inhibitor selections. For each selection, cells are selected from the population which by their reporter signal intensity behave differently than a main portion of the population. For example, cells may be selected from the population which fall outside of the mean reporter signal intensity for the population by a factor of two, three, four, five, ten or more.

The subpopulation of cells selected after each round of selection is expected to constitute a very small fraction of the cell population prior to the selection.

Cells that are selected during each selection round are washed free of the protein synthesis or protein degradation inhibitor and allowed to regenerate through cell division in culture. After regeneration, the cells may be subjected to further rounds of selection.

Gene recovery and sequence analysis may be performed on cells selected after one or more rounds of selection in order to identify the fusion protein expressed by the selected cells. Gene recovery and sequence analysis may be performed by any of a large number of well-known techniques.

6. Optional Further Selection of Cells

The selection process described in Section 5 serves to enrich the percentage of cells in the resulting population of selected cells that encode a short-lived protein. Optionally, further selection may be performed where individual clones of the selected cells are further analyzed for whether they encode a short-lived protein.

According to this variation, the selected cells are separated such that single cells are seeded into wells of microliter plates and allowed to grow, preferably to at least $10^4$ cells per well. The wells may then be treated with a protein synthesis or protein degradation inhibitor. Afterward, the individual wells are scanned to assess time-dependent changes in the reporter signal. Wells exhibiting time-dependent changes indicative of the cells expressing short-lived proteins may be marked and the cells contained therein recovered. Gene recovery and sequence analysis may then be performed on the recovered cells.

This additional selection of individual clones can be carried out manually with the aid of a fluorescent plate reader. Higher throughput may be desirable or even necessary if large numbers of cells need to be screened, for example, because the selection process yields a small population of desired cells. High throughput screening may be carried out using a Cellomics ArrayScan Kinetics HCS Workstation (Cellomics, Pittsburgh).

7. Validation of Selection Process

In order to validate the specificity of the selection process, cells that are selected may be analyzed using conventional methods to evaluate protein lability. For example, pulse-chase analysis may be performed to confirm whether the fusion protein expressed by the selected cells are short-lived. When GFP is used as the reporter protein, this validation may be performed by immunoprecipitating the labeled fusion protein with anti-GFP antisera, followed by SDS-PAGE and autoradiography.

8. Internal Standard For Monitoring Selection Efficiency

Stochastic cellular processes can induce the fluorescence signals of some cells to change over time. For example, changes in cell shape, cell cycle position, or intracellular redistribution of a fusion protein can all cause the fluorescent signal of a cell to change. When selecting cells based on a change in fluorescence, false positives may be selected lithe fluorescence signals of those cells change in a manner that causes the cells to be mistakenly selected as expressing short-lived fusion proteins.

Multiple rounds of population-based selections using FACS will serve to eliminate false positives misidentified as a result of such random fluctuations. False positive selections will also be eliminated in subsequent, more individualized screens.

It is nevertheless desirable to reduce the frequency with which false positives are at least initially selected. This can be achieved by using an internal standard whose signal also varies as a result of these stochastic cellular processes. As a result, by normalizing the reporter relative to the internal standard, a normalized reporter value can be determined that is more reliably indicative of the expression of the reporter.

For example, cells may be transformed or transfected so they express a fusion protein comprising the first reporter protein and a second reporter protein, such as beta-galactosidase, that has a different emission wavelength than the first reporter protein. This allows expression of the first reporter protein and the second reporter protein to be independently monitored. It also allows the signal from the first reporter protein for each cell to be normalized relative to the second reporter protein. The normalized reporter signal for a given cell should be less effected by the stochastic cellular processes of that cell. Hence, basing selection upon the normalized reporter signals for each cell should reduce the frequency of false positives.

The second reporter protein may be introduced into cells by any manner and by any vehicle. For example, the second reporter protein may also be introduced into the cell by transformation or transfection and may be introduced before, after, or with the introduction of the vector encoding the fusion protein.

In one embodiment, the vector library comprising the first reporter—cDNA fusion protein constructs further encodes the second reporter protein. Hence, initial selection of cells for whether the cells received a vector from the vector library may be based either upon the first reporter protein or the second reporter protein.

Optionally, cells may be added to each population which express a known short-lived protein as a benchmark. These benchmark cells for each population should have a brightness mode that is close to that of its related population. The benchmark cells may be added in known concentrations, for example in numbers that constitute 1:100, 1:1000 or 1:10,000 of total cells. The benchmark cells may also be marked with a benchmark reporter protein, such as beta-galactosidase. Since other cells in the population will not express the benchmark reporter protein, the effectiveness of the present invention to enrich the concentration of short-lived proteins relative to the initial cell library can be monitored by measuring the frequency of this marker.

9. Characterizing Sequence From cDNA Library in Selected Cells

After selecting cells whose reporter signal behavior indicates that the fusion protein is short-lived, the sequences encoding the fusion protein may be analyzed. Specifically, the selected cells may be pooled and extra-chromosomal DNA extracted and transfected into $E.$ $coli$. It is noted that other methods may be used to recover the gene inserts. For example, the gene inserts can be recovered through PCR, using flanking sequences from the vector used to introduce the sequence encoding the fusion protein as a primer.

The $E.$ $coli$ library produced by transfecting the extra-chromosomal DNA may then be used to obtain DNA sequence information. Individual bacterial cells may be isolated and cultured in commercially available 384-well high-density culture plates. Each individual culture plate may be bar-coded where individual clones are assigned a particular code. This allows the cell lines to be readily retrieved for further analysis. The barcode system may be implemented throughout the entire process.

$E.$ $coli$ cells in replica plates are diluted and used for DNA amplification in an appropriate 384-well PCR plate. After PCR amplification, the DNA fragments can be used for direct sequencing. A DNA sequence database may be established based on the sequence information. The DNA sequence and putative translated protein sequence can then be examined and compared with existing DNA sequence database using The National Center for Biotechnology Information (NCBI) and by using the BLAST program run by NCBI, or by The Protein Extraction Description and Analysis Tool (PDANT) program. Genes identified that are of interest may be readily retrieved from the original cell clones based on their barcodes.

10. Confirmation of Whether Isolated Proteins Are Short-Lived in Native Form

Once the DNA and protein sequences of the fusion proteins are identified, further analysis may be performed to evaluate whether the portion of the fusion protein encoded by the sequence from the cDNA library is short-lived in its native form, that is, when expressed free of the reporter protein. Testing of the lability of the native form of the protein screened via the above process may be performed by standard methods, such as pulse-chase analysis, which are known in the art.

11. Monitoring Changes in Degradation Rate of Proteins Under Different Conditions It is noted that the degradation rate of a given protein is itself subject to regulation. Hence, different proteins may be short-lived under certain cellular conditions and less labile under other conditions. FOr instance, IκB, the inhibitor of NFκB, forms a complex with NFκB and inhibits NFκB activity. When the pathway is triggered by TNF or IL-1, a cascade of kinases in the NFκB pathway is activated, which results in phosphorylation and degradation of IκB. NFκB is released from the complex and translocates from the cytoplasm to nucleus to mediate transcriptional induction of a number of genes whose products are very important to immunity and inflammatory responses.

A need thus exists for methodology that allows one to monitor how degradation rates of different proteins change under different conditions.

Figure 3:
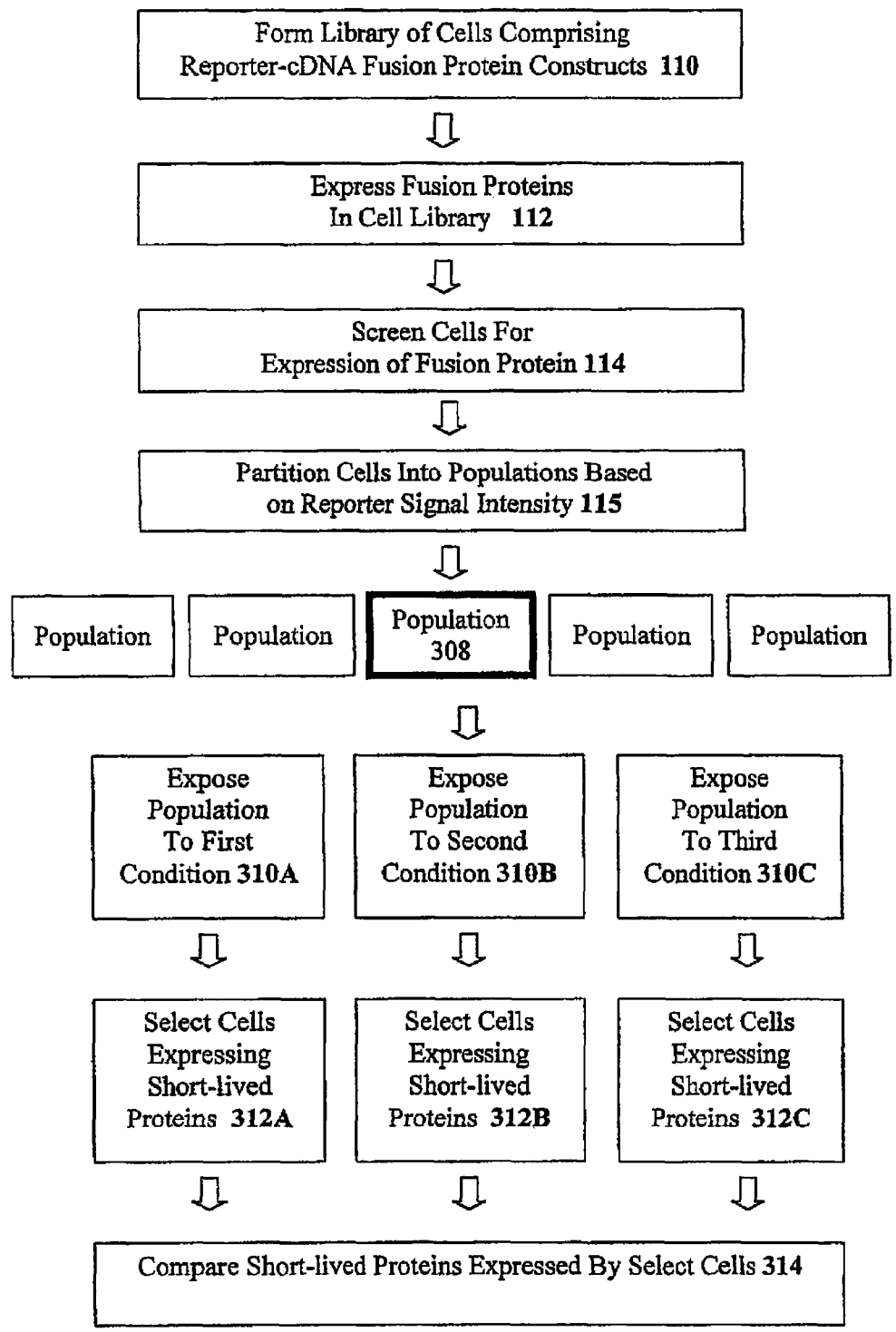
FIG. 3 illustrates a method for monitoring how degradation rates of different proteins change under different conditions.

FIG. 3 illustrates a method for monitoring how degradation rates of different proteins change under different conditions. According to this variation, a library of cells expressing a fusion protein library is formed 110, screened 114 and partitioned 115 according to the present invention.

One or more of the partitioned populations of cells 308 is then grown under different conditions 310A-310C which may serve to regulate protein degradation. These different conditions may include cell cycle position, inducing conditions or other factors. For example, the different conditions may include exposing the cells to a library of agents that may affect regulation of the degradation process.

Those cells that are found to have a reporter signal behavior indicative of a fusion protein being degraded as a short-lived protein are selected 312A-312C. The selection process may comprise the one or more selection rounds and other selection processes described above.

The fusion proteins expressed by the selected populations of cells 312A-312C are then compared 314. By seeing, which fusion proteins are expressed by the same population of cells 308, it is possible to determine how the different conditions influence protein degradation.

By comparing which proteins are degraded by the cells under different growth conditions and when exposed to different agents, the process of how the degradation of certain proteins is regulated can be elucidated. For example, by determining that a given protein is labile within a cell in the presence of a given agent but is otherwise a stable protein, one is able to begin to deduce how that protein is regulated. This information could lead to the identification and development of therapeutic agents that either reduce or increase the half life of selected proteins by knowing how to control the degradation regulatory pathway associated with that protein.

In some instances, conditions may affect the protein degradation of a group of proteins. By determining groups of proteins that appear to have their degradation rate linked in some way, regulatory pathways can be deduced. For example, the fact that administering an agent affects the degradation of a group of proteins may indicate that the agent is either inhibiting or inducing a given pathway. This allows the proteins involved in that pathway to be identified. By finding agents that inhibit different subgroups of proteins, the pathway may be further elucidated.

Being able to determine whether a given agent affects the degradation rate of more than one protein is very useful in designing therapeutics. For example, the fact that a given agent affects the degradation rate of multiple proteins may signal that that agent is not sufficiently selective and may cause undesirable side affects. The fact that a given agent affects the degradation rate of multiple proteins may also signal that that protein is not an attractive target for regulating a given pathway.

12. Comparing Short-Lived Protein Expression Across Different Samples

In Section 11, it was noted that the degradation rate of a given protein may be affected by the conditions under which the cells are grown. In that instance, a cDNA library isolated from a single sample is tested under different conditions.

This section describes how to compare which short-lived proteins are expressed by different cell samples. When the protein expression of normal cells and diseased cells are compared, it may be found that different short-lived proteins are either expressed or not expressed by the diseased cells. For example, the diseased cells may comprise a genetic abnormality relative to the normal cells. By comparing which short-lived proteins are expressed by normal and diseased cells, it may be possible to identify one or more short-lived proteins whose expression or non-expression account for the diseased cells being abnormal. Treatments may then be directed to these identified short-lived proteins.

Figure 4:
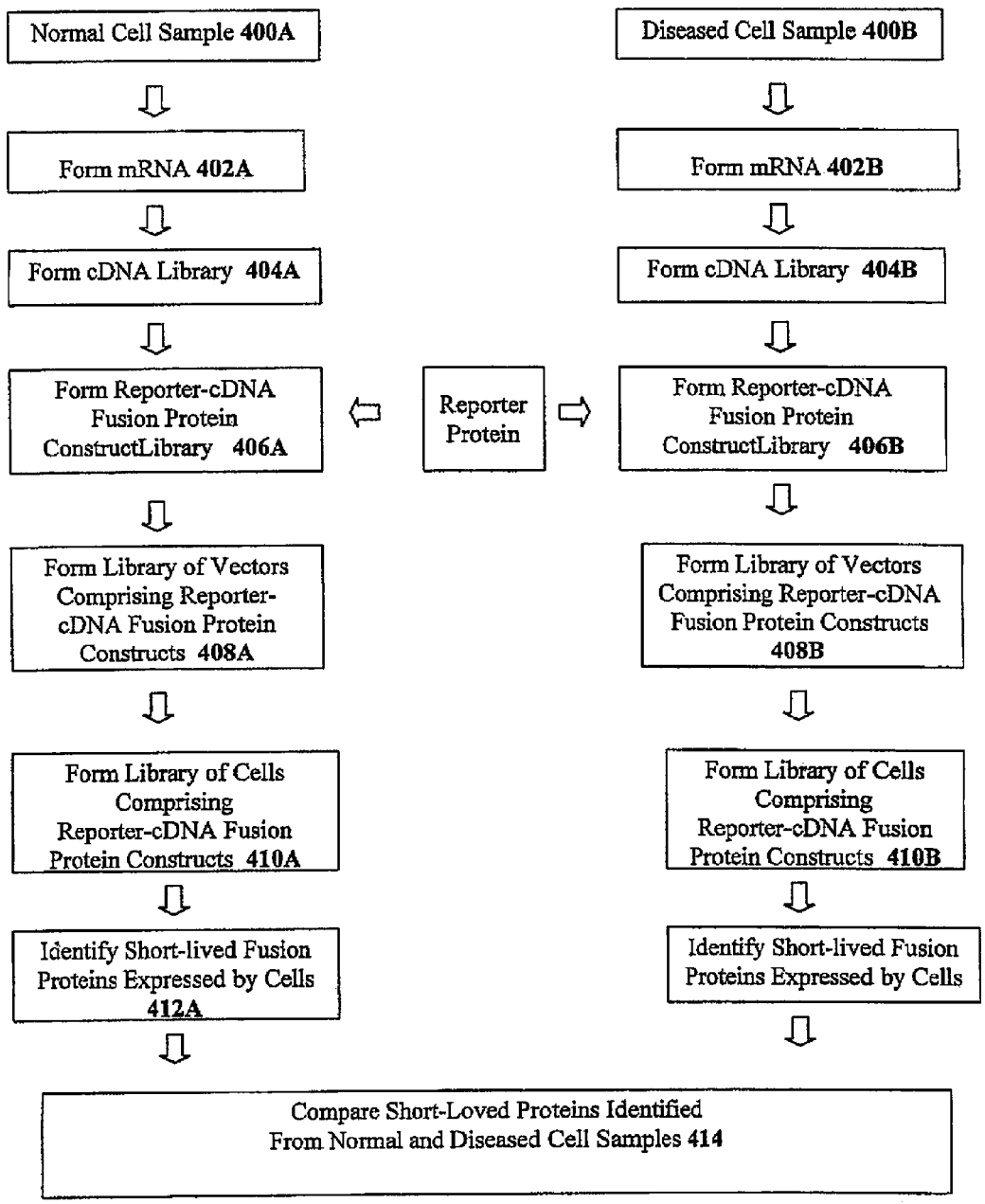
FIG. 4 illustrates an embodiment of a method for comparing which short-lived proteins are expressed by two or more different samples of cells.

FIG. 4 illustrates an embodiment of a method for comparing which short-lived proteins are expressed by two or more different samples of cells. In FIG. 4, a normal 400A and diseased 400B sample of cells are shown. mRNA libraries 402A, 402B and then cDNA libraries 404A, 404B are formed for the cell samples 400A, 400B. Libraries of constructs 406A, 406B, libraries of vectors 408A, 408B, and then libraries of cells 410A, 410B are formed based on each cDNA library. The resulting libraries of cells are then each processed as set forth in FIG. 1 in order to identify short-lived fusion proteins expressed by each library of cells 412A, 412B. By comparing 414 which short-lived fusion proteins are expressed by each library of cells 410A, 410B, it is possible to detect differences between the libraries and hence differences between the short-lived proteins expressed by the two or more different samples of cells 400A, 400B.

13. Method for Altering Degradation Rate For Short-Lived Proteins

Proteins differ widely in their lability, ranging from entirely stable to half-lives that measure minutes. In some cases, rapidly degraded proteins have been shown to contain an identifiable "degradation domain." Removal of this degradation domain makes such proteins stable and appending this domain to a stable protein changes its stability dramatically. Such a degradation domain has been identified in a number of short-lived proteins, such as the C terminus of mouse ODC. (Li, X., Stebbins, B., Hoffman, L., Pratt, G., Rechsteiner, M. and Coffino, P. (1996) The N Terminus of Antizyme Promotes Degradation of Heterologous Proteins. *The Journal of Biological Chemistry*, 271, 4441-4446; Loetscher, P., Pratt, G. and Rechsteiner, M. (1991) The C Terminus of Mouse Ornithine Decarboxylase Confers Rapid Degradation on Dihydrofolate Reductase. *The Journal of Biological Chemistry*, 266, 11213-11220) and the destruction box of cyclins (Glotzer, M., Murray, A. W. and Kirschner, M. W. (1991) Cyclin is Degraded by the Ubiquitin Pathway. *Nature*, 349, 132-138).

In some cases, the signal is a primary sequence such as the PEST sequence. Rechsteiner, M. and Rogers, S. W. (1996) PEST Sequences and Regulation by Proteolysis. *Trends in Biochemical Sciences*, 21, 267-271; Rogers, S., Wells, R. and Rechsteiner, M. (1986) Amino Acid Sequences Common to Rapidly Degraded Proteins: The PEST Hypothesis. *Science*, 234, 364-368. However, the structural features of such degradation domains are not sufficiently uniform as to provide a reliable guide to identifying the general class of labile proteins that interests us here. The major neutral protease responsible for degradation of labile regulatory proteins is the proteasome. Zwickl, P., Voges, D. and Baumeister, W. (1999) The Proteasome: A Macromolecular Assembly Designed for Controlled Proteolysis. *Philos Trans R Soc Lond B Biol Sci*, 354, 1501-11.

Prior to degradation, most short-lived proteins are covalently coupled to multiple copies of the 76 amino acid protein ubiquitin, a reaction catalyzed by a series of enzymes. Ciechanover, A. and Schwartz, A. L. (1998) The Ubiquitin-Proteasome Pathway: The Complexity and Myriad Functions of Proteins Death. *Proc Natl Acad Sci USA*, 95, 2727-30. These ubiquitinated proteins are recognized by 26S proteasome and degraded within its hollow interior. This system of regulated degradation is central to such processes as cell cycle progression, gene transcription and processing of antigens. A few proteins have been found to be exceptional. Verma, R. and Deshaies, R. J. (2000) A Proteasome Howdunit The Case of The Missing Signal. *Cell*, 101, 341-4. Like ornithine decarboxylase, they do not require ubiquitin modification for degradation by the proteasome.

A desirable utility of being able to rapidly and efficiently determine the sequence of a large number of different short-lived proteins is the prospect of identifying additional degradation domains. By knowing what domains affect recognition within the cell that a protein should be degraded, it is then possible to reengineer proteins either to increase or decrease their rate of degradation in vivo.

A significant problem in the art relates to the rate at which therapeutic proteins administered to the body are cleared. With enhanced knowledge regarding how protein degradation is regulated, for example, by better understanding what are the degradation domains of proteins, it is possible to modify the degradation domains of therapeutic proteins so that these proteins have longer half lives in the body when administered.

14. Compositions and Kits for Use in the Methods of the Present Invention

A wide variety of compositions and kits may be designed for use in combination with the various methods of the present invention. Various examples of these compositions, such as reporter—cDNA fusion protein construct libraries 106, vectors comprising the library of reporter—cDNA fusion protein constructs 108, and library of cells expressing the library of reporter—cDNA fusion proteins 110 have already been described herein.

It is noted that a variety of kits may be formed which may be used to construct these various compositions or which may be used in combination with these various compositions for performing aspects of the present invention. Several of these kits are described herein. Others will be well understood by one of ordinary skill in the art.

It will be apparent to those skilled in the art that various modifications and variations can be made in the compounds, compositions, kits, and methods of the present invention without departing from the spirit or scope of the invention. Thus, it is intended that the present invention cover the modifications and variations of this invention provided they come within the scope of the appended claims and their equivalents.

What is claimed is:

1. A method of identifying proteins degraded differently in different cells, the method comprising:
    providing a library of cells by introducing into one or more populations of cells vectors encoding proteins, wherein the proteins are encoded by sequences from the one or more cDNA libraries;
    expressing the proteins in the one or more populations of cells;
    separating the one or more populations of cells into a first subgroup of cells and a second subgroup of cells;
    inhibiting expression of the proteins in the first and second subgroups of cells;
    detecting protein degradation in the first and second subgroups of cells; and,
    comparing degradation of one or more proteins in the first subgroup of cells to the degradation of the one or more proteins in the second subgroup of cells;
    thereby identifying proteins with different degradation profiles in the cells.

2. The method of claim 1, wherein the encoded proteins are fusion proteins comprising a reporter.

3. The method of claim 2, wherein said comparing the protein degradation comprises identifying a lower reporter signal intensity in a subgroup as compared to that detected in another subgroup of cells, after inhibiting protein expression.

4. The method of claim 1, wherein said detecting comprises detecting a protein degradation rate over a period of time.

5. The method of claim 1, further comprising, the exposing first subgroup of cells and second subgroup of cells to different conditions, before said inhibiting of expression.

6. The method of claim 5, wherein the different conditions comprise conditions selected from the group consisting of: culture conditions, growth conditions, exposure to agents, exposure to a library of agents, and exposure to therapeutic agents.

7. The method of claim 5, further comprising identifying patterns of two or more different proteins that have their degradation influenced by a condition.

8. The method of claim 1, wherein the one or more cDNA libraries is a cDNA library from a single type of cells.

9. The method of claim 1, wherein said comparing comprises identifying one or more proteins that are short-lived in the first subgroup and one or more proteins that are short-lived in the second subgroup.

10. The method of claim 1, wherein the one or more cDNA libraries comprise two different cDNA libraries.

11. The method of claim 10, wherein the two different cDNA libraries are prepared from different cells.

12. The method of claim 11, wherein the different cells comprise healthy cells and diseased cells.

13. The method of claim 12, further comprising identifying proteins associated with the disease of the diseased cell.

14. A method of identifying proteins that have their degradation linked to a common condition in a cell, the method comprising:
    providing one or more cDNA libraries;
    providing a library of cells by introducing into a population of cells vectors encoding proteins, wherein the proteins are encoded by sequences from the one or more cDNA libraries;
    expressing the proteins in the population of cells;
    exposing the population of cells to a culture condition;
    inhibiting expression of the proteins in the population of cells;
    detecting protein degradation in the population of cells; and,
    identifying a group of proteins with degradation influenced by the culture condition;
    thereby identifying proteins that have their degradation linked to a common condition.

15. The method of claim 13, wherein the encoded proteins are fusion proteins comprising a reporter.

16. The method of claim 14, wherein the condition is selected from the group consisting of: growth conditions, exposure to an agent, exposure to a library of agents, and exposure to a therapeutic agent.

17. The method of claim 14, wherein said detecting comprises detecting a protein degradation rate over a period of time.

18. The method of claim 14, wherein said detecting comprises detecting two or more short-lived proteins.

19. The method of claim 14, further comprising elucidating a regulatory pathway based on the proteins identified.

20. A method for identifying differences in short-lived proteins associated with different cell samples, the method comprising:
- providing a first cDNA library from a sample of first cells and a second cDNA library from a sample of second cells, which first cells are different from the second cells;
- providing a first library of cells expressing sequences encoded by the first cDNA library;
- providing a second library of cells expressing sequences encoded by the second cDNA library;
- inhibiting expression proteins in the first library of cells and in the second library of cells;
- detecting the protein degradation in the first library of cells and in the second library of cells;
- identifying one or more proteins that are short-lived in the first library of cells and one or more proteins that are short-lived in the second library of cells; and
- comparing the identified short-lived proteins between the first library of cells and second library of cells, thereby identifying short-lived proteins associated with cell sample differences.

21. The method of claim 20, wherein the first cells are healthy cells and the second cells are diseased cells.

22. The method of claim 20, wherein the encoded proteins are fusion proteins comprising a reporter.

23. The method of claim 20, wherein said detecting comprises detecting a protein degradation rate over a period of time.

* * * * *